United States Patent [19]

Duvert

[11] Patent Number: 5,565,481
[45] Date of Patent: Oct. 15, 1996

[54] FUNGICIDES COMPRISING IPRODIONE AND A TRIAZOLE

[75] Inventor: Patrice Duvert, Lyons, France

[73] Assignee: Rhone-Poulenc Agrochimie, Lyon Cedex, France

[21] Appl. No.: 372,146

[22] Filed: Jan. 13, 1995

[30] Foreign Application Priority Data

Jan. 14, 1994 [FR] France ................................ 94 00565

[51] Int. Cl.⁶ .......................... A01N 43/50; A01N 43/64
[52] U.S. Cl. ........................................... 514/383; 514/391
[58] Field of Search ..................................... 514/391, 383

[56] References Cited

U.S. PATENT DOCUMENTS 5,420,148   5/1995   Dehne et al. ........................... 514/395

FOREIGN PATENT DOCUMENTS

| 587096 | 8/1989 | Australia . |
|---|---|---|
| 67980/90 | 6/1991 | Australia . |
| 0230844 | 8/1987 | European Pat. Off. . |
| 0433194 | 6/1991 | European Pat. Off. . |
| 0511167 | 10/1992 | European Pat. Off. . |
| 2516350 | 5/1983 | France . |
| 2110934 | 6/1983 | United Kingdom . |

OTHER PUBLICATIONS

*Chemical Abstracts*, vol. 104, No. 1, Jan. 6, 1986, abstract No. 2081.
Worthing et al, The Pesticide Manual, 9th Ed. (1991) p. 501.
Anon, C. A. vol. 112 (1990), 112:50497u.

*Primary Examiner*—Allen J. Robinson
*Attorney, Agent, or Firm*—Burns, Doane, Swecker & Mathis, L.L.P.

[57] ABSTRACT

(1) Fungicidal combinations and compositions, comprising a compound A of the formula:

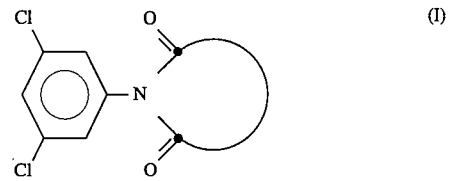

wherein the symbol

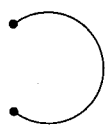

represents

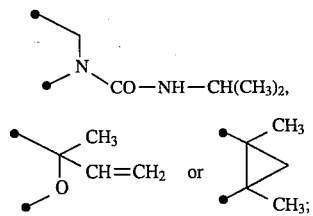

and a compound B chosen from bromuconazole, tebuconazole, epoxiconazole, cyproconazole, flusilazole, metconazole, hexaconazole and difenoconazole.

(2) Process for treating crops using these combinations/compositions.

17 Claims, No Drawings

FUNGICIDES COMPRISING IPRODIONE AND A TRIAZOLE

The subject of the present invention is a fungicidal combination or composition which is useful for treating fungal attacks on crops and which is based on a compound whose formula comprises a triazole group. It also relates to a process for treating crops having the same aim.

Compounds whose formula comprises a triazole group are well-known to farmers, especially for their effectiveness against the group of diseases which affect or are capable of affecting barley, such as powdery mildew, rust, rhynchosporium disease and helminthosporium disease.

However, the effectiveness of these compounds against helminthosporium disease is often considered to be insufficient.

As a matter of fact, this last-mentioned disease has become much more prevalent in recent years due to changes in cultivation methods, such as intensification of cultivation, with the increase in the input of nitrogenous fertilizers, and due to the adoption, by an increasing number of farmers, of the cultivation of winter barley.

It is, moreover, always desirable to reduce the doses of chemicals distributed in the environment for treating fungal diseases of crops, especially by reducing the application doses of the chemicals, and to widen the possibilities of choice offered to the farmer, in order for the latter to find the solution which is best suited to his particular problem.

An aim of the invention is thus to provide a new fungicidal combination or composition which is useful for the problem described above.

Another aim of the invention is to propose a new fungicidal combination or composition which is useful in the preventive or curative treatment of powdery mildew, rust or rhynchosporium disease.

Another aim of the invention is to propose a fungicidal combination or composition which has improved effectiveness, preventively or curatively, against helminthosporium disease of barley.

It has now been found that these aims could be achieved in all or in part by virtue of the fungicidal combination or composition according to the present invention, which makes it possible to observe noteworthy synergistic effects.

The fungicidal combination and the fungicidal composition according to the invention comprise a fungicidally effective amount of a compound A, corresponding to the formula (I):

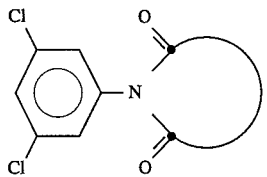
(I)

wherein the symbol

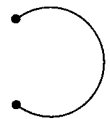

represents

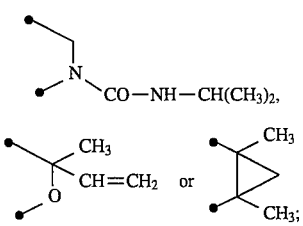

and a compound B chosen from bromuconazole, tebuconazole, epoxiconazole, cyproconazole, flusilazole, metconazole, hexaconazole and difenoconazole. The fungicidal composition of the invention further comprises an agriculturally acceptable vehicle and/or an agriculturally acceptable surface-active agent.

The compound A, as defined above, corresponds to one of the following active materials: iprodione, vinclozolin or procymidone.

Bromuconazole is 1-[4-bromo-2-(2,4-dichlorophenyl)tetrahydro-2-furylmethyl]-1H-1,2,4-triazole, which is described in European Patent Publication No. 0246982. Epoxiconazole is (2RS,3SR)-1-[3-(2-chlorophenyl)-2-(4-fluorophenyl)oxiran-2-ylmethyl]-1H-1,2,4-triazole, which is described in at least one of the two European Patent Publication Nos. 0094564 and 0196038. Metconazole is (1RS,5RS)-5-(4-chlorobenzyl)-2,2-dimethyl-1-(1H-1,2,4-triazol-1-ylmethyl)cyclopentanol, which is described in European Patent Publication No. 0267778. The other active materials mentioned above are described in the work: "The Pesticide Manual", 9th Edition, by Charles R. Worthing and Raymond J. Hance, published by the British Crop Protection Council.

Tebuconazole is (RS)-1-(4-chlorophenyl)-4,4-dimethyl-3-(1H-1,2,4-triazol-1-ylmethyl)pentan-3-ol. Cyproconazole is (2RS,3RS;2RS,3SR)-2-(4-chlorophenyl)-3-cyclopropyl-1-(1H-1,2,4-triazol-1-yl)butan-2-ol. Flusilazole is 1-[[bis(4-fluorophenyl)(methyl)silyl]methyl]-1H-1,2,4-triazole. Hexaconazole is (RS)-2-(2,4-dichlorophenyl)-1-(1H-1,2,4-triazol-1-yl)hexan-2-ol. Difenoconazole is cis, trans-3-chloro-4-[4-methyl-2-(1H-1,2,4-triazol-1-ylmethyl)-1,3-dioxolan-2-yl phenyl 4-chlorophenyl ether.

The combination of the invention and the composition of the invention comprising this combination are useful for treating fungal diseases of various crops. They are thus effective in treating powdery mildew, rust, rhynchosporium disease or helminthosporium disease of barley or in treating powdery mildew, rusts, septoria diseases and fusarium diseases of wheat. They are also effective in controlling grey mould, alternaria disease, sclerotinia disease, cercospora disease, helminthosporium disease and fusarium disease of proteinaceous and oleaginous plants (especially pea, oilseed rape and maize), as well as for treating diseases of the lawn such as rust, fusarium disease, sclerotinia disease and rhizoctonia disease. Moreover, they are effective in controlling alternaria disease, powdery mildew and monilia disease of fruit trees and for controlling alternaria disease of vegetable crops comprising, especially, potato, tomato, radish and carrot.

The compound B/compound A ratio by weight in the combination or composition according to the invention is generally between about 0.05 and about 10, preferably between about 0.08 and about 3, and more preferentially still between about 0.1 and about 1.

According to an advantageous variant of the invention, the compound B included in the combination or composition according to the invention is chosen from bromuconazole, tebuconazole, epoxiconazole and flusilazole.

According to another advantageous variant of the invention, the compound A included in the combination or composition according to the invention is 3-(3,5-dichlorophenyl)-N-isopropyl-2,4-dioxoimidazolidine-1-carboxamide, also known as iprodione.

According to yet another advantageous variant of the invention, the compound B included in the combination or composition according to the invention is bromuconazole.

The combination or composition resulting from these last two variants taken simultaneously is particularly advantageous due to its outstanding activity with respect to phytopathogenic fungi, especially for diseases of barley, and due to its selectivity with respect to crops.

The combinations and compositions according to the invention are again advantageous due to the spectrum of activity and the low doses which can be used for the active materials, this last quality being particularly important for easily understandable ecological reasons.

The fungicidal composition according to the invention generally contains from about 0.5 to about 95% of a mixture of the compound A and the compound B.

It can be the concentrated composition, that is to say the commercial product combining the two active materials. It can also be the dilute composition ready to be sprayed on the crop to be treated. In this latter case, dilution with water can be carried out either from a commercial concentrated composition containing the two active materials (this mixture being known as "ready mix") or by means of the mixture prepared at the time of use (known as "tank mix") of two commercial concentrated compositions each containing one active material.

The composition according to the invention can additionally comprise all the usual additives or adjuvants of plant-protection compositions, especially vehicles, surface-active agents, adhesion agents and flow-improving agents.

In the present account, the term "vehicle" denotes a natural or synthetic, organic or inorganic material with which the active materials are combined to facilitate their application on the plant. This vehicle is thus generally inert and it must be acceptable in agriculture, especially on the treated plant. The vehicle can be solid (clays, natural or synthetic silicates, silica, resins, waxes, solid fertilizers and the like) or liquid (water, alcohols, ketones, petroleum fractions, aromatic or paraffinic hydrocarbons, chlorinated hydrocarbons, liquefied gases, and the like).

The surface-active agent can be an emulsifying, dispersing or wetting agent of ionic or nonionic type. There may be mentioned, for example, salts of polyacrylic acids, salts of lignosulfonic acids, salts of phenolsulfonic or naphthalenesulfonic acids, polycondensates of ethylene oxide with fatty alcohols or with fatty acids or with fatty amines, substituted phenols (especially alkylphenols or arylphenols), salts of esters of sulfosuccinic acids, taurine derivatives (especially alkyltaurates) or phosphoric esters of polyoxyethylenated phenols or alcohols. The presence of at least one surface-active agent is desirable to promote dispersion of the active materials in water and their ready application on the plants.

The composition of the invention can also contain any kind of other ingredients such as, for example, protective colloids, adhesives, thickening agents, thixotropic agents, penetrating agents, stabilizing agents, sequestering agents, pigments, dyes or polymers.

More generally, the composition according to the invention can include all the solid or liquid additives corresponding to the usual techniques for the formulation of plant-protection products.

The composition according to the invention can be in the solid, gel or liquid form and, in the latter case, in the form of solutions or suspensions or emulsions or emulsifiable concentrates. Liquid compositions are preferred, due both to their convenience of use and to their simplicity of manufacture.

There may be mentioned, as forms of solid compositions, powders for dusting or dispersion (with an active compounds content which can range up to 100%), wettable powders and granules for dry spreading, as well as dispersible or soluble granules.

Wettable powders (or powders to be sprayed), as well as dispersible granules, generally contain 20 to 95% of active materials and, in addition to the solid vehicle, from 0 to 5% of a wetting agent, from 3 to 10% of a dispersing agent and, when necessary, from 0 to 10% of one or more stabilizing agents and/or other additives, such as pigments, dyes, penetrating agents, adhesives, or antidumping agents, dyes, and the like. It is well understood that some of these compositions, such as wettable powders or dispersible granules, are intended to constitute liquid compositions at the time of application.

There may be mentioned, as forms of liquid compositions, solutions, in particular water-soluble concentrates, emulsifiable concentrates, emulsions, suspension concentrates, aerosols or pastes.

The emulsifiable or soluble concentrates most often comprise 10 to 80% of active materials, the emulsions or solutions ready for application containing, for their part, 0.01 to 20% of active materials. In addition to the solvent, the emulsifiable concentrates can contain, when necessary, 2 to 20% of suitable additives such as the stabilizing agents, surface-active agents, penetrating agents, corrosion inhibitors, dyes or adhesives mentioned above. From these concentrates, it is possible to obtain, by dilution with water, emulsions of any desired concentration, which are particularly suitable for application on the aerial parts of the plant to be treated. As has already been said, aqueous dispersions and emulsions, for example the compositions obtained by diluting a wettable powder or an emulsifiable concentrate according to the invention with water, come within the general scope of the present invention. The emulsions can be of the water-in-oil or oil-in-water type and they can have a thick consistency, like that of a "mayonnaise".

The suspension concentrates, also applicable by spraying, are a stable fluid product, which does not thicken or form a sediment after storage, and they generally contain from 10 to 75% of active materials, from 0.5 to 15% of surface-active agents, from 0.1 to 10% of thixotropic agents and from 0 to 10% of suitable additives, such as pigments, dyes, antifoaming agents, corrosion inhibitors, stabilizing agents, penetrating agents and adhesives and, as vehicle, water or an organic liquid in which the active materials are insoluble or nearly insoluble: certain organic solid materials or inorganic salts can be dissolved in the vehicle to aid in preventing sedimentation or as antigels for water.

The composition according to the invention is prepared according to processes known per se.

Thus, to obtain powders to be sprayed or wettable powders, the active materials are intimately mixed, in suitable mixers, with the additional substances and the mixture is milled with mills or other grinders. Powders to be sprayed are thereby obtained with advantageous wettability and suspensibility; they can be suspended in water at any desired concentration and these suspensions can be used very advantageously, in particular for application on the aerial parts of the plants.

Pastes or suspension concentrates can be produced in place of wettable powders. The conditions and modes of production and use of these pastes are similar to those of wettable powders or powders to be sprayed, part of the milling operation necessary simply being carried out in a liquid medium.

The dispersible granules are generally prepared by agglomeration or extrusion or compacting, in suitable granulation systems, of compositions of wettable powder type. The granules for dry spreading are generally obtained by impregnating a granulated vehicle with a solution or an emulsion of the active materials.

The invention finally relates to a treatment process intended to control or prevent fungal attacks on crops, characterized in that an effective and non-phytotoxic dose of a combination or composition according to the invention is applied on the aerial parts of the plants.

These combinations and compositions are advantageously used so that the dose applied of the mixture of the compounds A and B is between about 5 and about 5000 g/ha and preferably between about 150 and about 3000 g/ha. This dose is a function of the plant treated, the degree of infestation and the weather conditions.

Mention may be made among the crops which are suitable for the treatment process according to the invention, of cereals, especially barley and wheat; proteinaceous and oleaginous plants, such as peas, oilseed rape, sunflower and maize; the lawn; fruit trees and vegetable crops comprising especially potato, tomato, radish and carrot. Barley is a preferred crop for the treatment process according to the invention.

The following examples are given as nonlimiting examples of the advantageous properties of the combinations and compositions according to the invention.

In these examples, the compound A is iprodione and the compound B is 1-[4-bromo-2-(2,4-dichlorophenyl)tetrahydro-2-furylmethyl]-1H-1,2,4-triazole, also known as bromuconazole.

EXAMPLE 1

In Vitro Test of a Composition Comprising a Mixture of Bromuconazole and Iprodione on *Dreschlera teres* Responsible for Helminthosporium Disease of Barley A nutrient medium consisting of maize flour and gelose is introduced in the supercooled state into a series of petri dishes (20 ml per dish).

During the filling of the dishes, injection is carried out of 200 µl of a solution of the active materials to be tested (alone or as a mixture) in acetone, so as to obtain the desired final concentration.

Petri dishes analogous to the above, into which similar amounts of a nutrient medium not containing active material are poured, are used as control.

After 24 hours, a pellet with a diameter of 5 mm, comprising a fragment of mycelium, withdrawn from a *Dreschlera teres* stock culture, is deposited at the center of each dish. The petri dishes are stored at 20° C. for 1 week.

The growth of the fungus (measured by the diameter of the mycelial growth) in the dishes containing the active material or the mixture of active materials to be tested is then compared with that of this same fungus in the dish used as control.

The degree of inhibition of the fungus, expressed as a percentage, is thus determined for each active material or mixture of active materials, at the dose shown.

The degree of inhibition results collated in the table below correspond to the mean of three repetitions.

| BROMUCONAZ | DEGREE OF INHIBITION AS % | | | | | | |
|---|---|---|---|---|---|---|---|
| | IPRODIONE (mg/l) | | | | | | |
| OLE (mg/l) | 0 | 0.06 | 0.125 | 0.25 | 0.5 | 1 | 2 |
| 0 | 0 | 8.2 | 3.2 | 21.7 | 39.2 | 49.2 | 49.2 |
| 0.03 | 15.7 | | | | | | |
| 0.06 | 14.2 | | 16.7 | | | | |
| 0.125 | 17.5 | 26.8 | 30 | 42.5 | | | |
| 0.25 | 40 | | 49.3 | 56.7 | 68.2 | | |
| 0.5 | 56.7 | | | 81.3 | 75.7 | 89 | |
| 1 | 68.2 | | | | 75.8 | 90.7 | 100 |

EXAMPLE 2

In Vivo Test of a Composition Comprising a Mixture of Bromuconazole and Iprodione on *Alternaria brassicae,* Responsible for Alternaria Disease of Radish A suspension is prepared comprising bromuconazole and/or iprodione in a liquid mixture consisting of 0.3 ml of a surface-active agent (oleate of polyoxyethylenated derivative of sorbitan) diluted to 10% in water and of 40 ml of water. The dose(s) of the active material(s) is/are shown in the table below.

Radish seedlings are grown in pots filled with peat/pozzolana. When these seedlings have reached the stage of development of the first visible leaf, they are treated by spraying with the above suspension.

After 24 hours, each seedling is infected by spraying by means of an aqueous suspension of *Alternaria brassicae* spores (400,000 sp/cm$^3$).

After this infection, the radish seedlings are incubated for 9 days at approximately 20° C. in an atmosphere saturated with moisture.

The results are then read, by comparison with radish seedlings infected without having received fungicidal treatment, known as control seedlings.

The fungicidal efficiency, expressed as a percentage, which is shown in the table below, is thus determined for each active material or mixture of active materials, at the dose shown.

| BROMUCONAZOLE | FUNGICIDAL EFFICIENCY AS % | | | | | |
|---|---|---|---|---|---|---|
| | IPRODIONE (mg/l) | | | | | |
| (mg/l) | 0 | 6 | 12 | 25 | 50 | 100 |
| 0 | 0 | 5 | 15 | 92.5 | 98.2 | 99.5 |
| 25 | 2.5 | 30 | 77.5 | 95 | 99 | 99.5 |
| 50 | 7.5 | | 90 | 92.5 | 97.5 | 100 |
| 100 | 27.5 | | | 97.5 | 100 | 100 |
| 200 | 86.2 | | | | 97 | |

EXAMPLE 3

In Vitro Test of a Composition Comprising a Mixture of Bromuconazole and Iprodione on *Sclerotinia homeocarpa,* Responsible for Sclerotinia Disease, or Dollar Spot, of the Lawn A nutrient medium consisting of a mixture of agar, dextrose and starch is introduced in the supercooled state into a series of petri dishes (20 ml per dish).

During the filling of the dishes, the injection is carried out of 200 µl of a solution of the active materials to be tested (alone or as a mixture) in acetone, so as to obtain the desired final concentration (shown in the table below).

Petri dishes analogous to the above, into which similar amounts of a nutrient medium not containing active material are poured, are used as control.

After 24 hours, a pellet with a diameter of 5 mm, comprising a fragment of mycelium, withdrawn from a *Sclerotinia homeocarpa* stock culture, is deposited at the center of each dish. The petri dishes are stored at 20° C. for 4 days.

The growth of the fungus (measured by the diameter of the mycelial growth) in the dishes containing the active material or the mixture of active materials to be tested is then compared with that of this same fungus in the dish used as control.

The degree of inhibition of the fungus, expressed as a percentage, which is shown in the following table, is thus determined for each active material or mixture of active materials, at the dose shown:

| DEGREE OF INHIBITION AS % | | | | |
|---|---|---|---|---|
| | IPRODIONE (mg/l) | | | |
| BROMUCONAZOLE (mg/l) | 0 | 0.25 | 0.5 | 1 |
| 0 | 0 | 0 | 0 | 89.3 |
| 0.06 | 26.2 | 60.5 | | |
| 0.125 | 26.2 | 66.3 | 83.6 | |
| 0.25 | 32.8 | 72 | 74.1 | 99.4 |
| 0.5 | 82.7 | 98 | 85.6 | 88.5 |
| 1 | 98 | 99.4 | 99.4 | 100 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A fungicidal combination comprising synergistic fungicidally effective amounts of compound A which is iprodione and compound B which is bromuconazole, wherein the compound B/compound A ratio by weight is between about 0.25 and about 4.

2. A method for the control or prevention of fungal disease in plants, said method comprising applying to the aerial parts of the plants a synergistic fungicidally effective, non-phytotoxic amount of a fungicidal combination according to claim 1.

3. The method according to claim 2, wherein compounds A and B are applied in a combined dose of between about 5 and about 5000 g/ha.

4. The method according to claim 3, wherein compounds A and B are applied in a combined dose of between about 150 and about 3000 g/ha.

5. The method according to claim 2, wherein the plants treated are cereals, proteinaceous or oleaginous plants, lawn, fruit trees or vegetable crops.

6. The method according to claim 5, wherein the plants treated are barley plants.

7. A fungicidal combination comprising synergistic fungicidally effective amounts of compound A which is iprodione and compound B which is bromuconazole, wherein the compound B/compound A ratio by weight is between about 0.25 and about 1.

8. The fungicidal combination according to claim 7, wherein the compound B/compound A ratio by weight is about 0.5.

9. A fungicidal composition comprising:
   (1) synergistic fungicidally effective amounts of compound A which is iprodione and compound B which is bromuconazole, wherein the compound B/compound A ratio by weight is between about 0.25 and about 4; and
   (2) at least one member of the group consisting of an agriculturally acceptable vehicle and an agriculturally acceptable surface-active agent.

10. The fungicidal composition according to claim 9, wherein the compound B/compound A ratio by weight is between about 0.25 and about 1.

11. The fungicidal composition according to claim 10, wherein the compound B/compound A ratio by weight is about 0.5.

12. The fungicidal composition according to claim 9, wherein compound A and compound B together constitute from about 0.5 to about 95% of the composition.

13. A method for the control or prevention of fungal disease in plants, said method comprising applying to the aerial parts of the plants a synergistic fungicidally effective, non-phytotoxic amount of a fungicidal composition according to claim 9.

14. The method according to claim 13, wherein compounds A and B are applied in a combined dose of between about 5 and about 5000 g/ha.

15. The method according to claim 14, wherein compounds A and B are applied in a combined dose of between about 150 and about 3000 g/ha.

16. The method according to claim 13, wherein the plants treated are cereals, proteinaceous or oleaginous plants, lawn, fruit trees or vegetable crops.

17. The method according to claim 16, wherein the plants treated are barley plants.

* * * * *